(12) United States Patent
Miyaki

(10) Patent No.: US 9,636,087 B2
(45) Date of Patent: May 2, 2017

(54) ULTRASOUND OBSERVATION APPARATUS, METHOD FOR OPERATING ULTRASOUND OBSERVATION APPARATUS, AND COMPUTER-READABLE RECORDING MEDIUM

(71) Applicant: OLYMPUS CORPORATION, Tokyo (JP)

(72) Inventor: Hironaka Miyaki, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/148,046

(22) Filed: May 6, 2016

(65) Prior Publication Data
US 2016/0242743 A1     Aug. 25, 2016

Related U.S. Application Data

(63) Continuation of application No. PCT/JP2014/078998, filed on Oct. 24, 2014.

(30) Foreign Application Priority Data

Jan. 24, 2014    (JP) ................................ 2014-011840

(51) Int. Cl.
*A61B 8/08*     (2006.01)
*A61B 8/00*     (2006.01)
(Continued)

(52) U.S. Cl.
CPC .............. *A61B 8/5223* (2013.01); *A61B 8/08* (2013.01); *A61B 8/4461* (2013.01);
(Continued)

(58) Field of Classification Search
CPC ... A61B 8/5223; A61B 8/5207; A61B 8/5246; A61B 8/463; A61B 8/4461; A61B 8/4477
See application file for complete search history.

(56) References Cited

U.S. PATENT DOCUMENTS

| 8,619,142 B2 | 12/2013 | Miyaki |
| 2012/0310087 A1 | 12/2012 | Miyaki et al. |
| 2015/0148678 A1 | 5/2015 | Hashiba et al. |

FOREIGN PATENT DOCUMENTS

| JP | 5114609 B2 | 1/2013 |
| JP | 2013-056033 A | 3/2013 |

(Continued)

OTHER PUBLICATIONS

International Search Report dated Feb. 10, 2015 issued in PCT/JP2014/078998.

(Continued)

*Primary Examiner* — Bo J Peng
(74) *Attorney, Agent, or Firm* — Scully, Scott, Murphy & Presser, P.C.

(57) ABSTRACT

An ultrasound observation apparatus includes: a first generation unit that computes a received signal based on first and second echo signals obtained by transmitting ultrasound signals having different phases along a same line to a specimen and reflection of the ultrasound signals from the specimen, and generates a first ultrasound image having first display mode, using the received signal; an extraction unit that calculates first and second features based on frequency spectra of the first and second echo signals, and extracts a third feature from the first and second features so as to be associated with a pixel position in image; a second generation unit that generates a second ultrasound image having second display mode at a pixel position where the third feature is not less than threshold; and a composition unit that generates a composite image by combining the first and second ultrasound images at the pixel position.

11 Claims, 14 Drawing Sheets

(51) Int. Cl.
  *G01S 7/52* (2006.01)
  *G01S 15/89* (2006.01)
(52) U.S. Cl.
  CPC ............ *A61B 8/4477* (2013.01); *A61B 8/463* (2013.01); *A61B 8/5207* (2013.01); *A61B 8/5246* (2013.01); *G01S 7/52033* (2013.01); *G01S 7/52038* (2013.01); *G01S 15/8963* (2013.01)

(56) References Cited

FOREIGN PATENT DOCUMENTS

WO    WO 2012/063976 A1    5/2012
WO    WO 2014/007100 A1    1/2014

OTHER PUBLICATIONS

Japanese Office Action dated Sep. 24, 2015 issued in JP 2015-527391.
Abstract only of WO 2012/133878 A1, dated Oct. 4, 2012.

ULTRASOUND OBSERVATION APPARATUS, METHOD FOR OPERATING ULTRASOUND OBSERVATION APPARATUS, AND COMPUTER-READABLE RECORDING MEDIUM

CROSS REFERENCES TO RELATED APPLICATIONS

This application is a continuation of PCT international application Ser. No. PCT/JP2014/078998, filed on Oct. 24, 2014 which designates the United States, incorporated herein by reference, and which claims the benefit of priority from Japanese Patent Application No. 2014-011840, filed on Jan. 24, 2014, incorporated herein by reference.

BACKGROUND

1. Technical Field

The disclosure relates to an ultrasound observation apparatus for observing tissue of a specimen using ultrasound waves, a method for operating the ultrasound observation apparatus, and a computer-readable recording medium.

2. Related Art

In ultrasound observation techniques, there is known THI (tissue harmonic imaging) that performs image generation using the nonlinearity of body tissue (see, for example, JP 2013-56033 A). THI is a technique in which a plurality of ultrasound signals having different phases or amplitudes are sequentially transmitted, and received signals that represent ultrasound echoes of the ultrasound signals are subjected to addition, subtraction, or the like, by which a signal whose harmonic component is enhanced is obtained, and based on the signal an image is generated. According to THI, an ultrasound image with improved resolution and reduced artifacts can be obtained.

On the other hand, there is also known a technique in which a feature image that represents differences in tissue characteristics of body tissue is generated using frequency feature of ultrasound scattered in body tissue (see, for example, JP 5114609 B2). In this technique, a frequency spectrum is computed by performing frequency analysis by performing fast Fourier transform (FFT) on a received signal representing an ultrasound echo, and a feature image is generated based on feature which is extracted by, for example, performing an approximation process on the frequency spectrum.

SUMMARY

In some embodiments, an ultrasound observation apparatus includes: an ultrasound probe configured to transmit a first ultrasound signal and a second ultrasound signal to a specimen along a same line, and to receive first and second ultrasound echo signals generated by reflection of the first and second ultrasound signals from the specimen, the second ultrasound signal having a different phase or amplitude from the first ultrasound signal; a first image data generation unit configured to perform a calculation process on first and second received signals, which respectively correspond to the first and second ultrasound echo signals, to compute a third received signal, and to generate image data of a first ultrasound image having a predetermined display mode, using the third received signal; a feature extraction unit configured to: calculate a first feature based on a frequency spectrum of the first ultrasound echo signal; calculate a second feature based on a frequency spectrum of the second ultrasound echo signal; and extract a third feature from the calculated first and second features so as to be associated with a pixel position in the first ultrasound image; a second image data generation unit configured to generate image data of a second ultrasound image having a second display mode different from the predetermined display mode, at a pixel position where the third feature is not less than or not more than a predetermined threshold; and an image composition unit configured to generate image data of a composite image by combining the first ultrasound image with the second ultrasound image at the pixel position where the third feature is not less than or not more than the predetermined threshold.

In some embodiments, a method for operating an ultrasound observation apparatus is provided. The ultrasound observation apparatus has an ultrasound probe configured to transmit a first ultrasound signal and a second ultrasound signal to a specimen along a same line, and to receive first and second ultrasound echo signals generated by reflection of the first and second ultrasound signals from the specimen, the second ultrasound signal having a different phase or amplitude from the first ultrasound signal. The method includes: by a first image data generation unit, performing a calculation process on first and second received signals, which respectively correspond to the first and second ultrasound echo signals, to compute a third received signal, and generating image data of a first ultrasound image having a predetermined display mode, using the third received signal; by a feature extraction unit: calculating a first feature based on a frequency spectrum of the first ultrasound echo signal; calculating a second feature based on a frequency spectrum of the second ultrasound echo signal; and extracting a third feature from the calculated first and second features so as to be associated with a pixel position in the first ultrasound image; generating, by a second image data generation unit, image data of a second ultrasound image having a second display mode different from the predetermined display mode, at a pixel position where the third feature is not less than or not more than a predetermined threshold; and generating, by an image composition unit, image data of a composite image by combining the first ultrasound image with the second ultrasound image at the pixel position where the third feature is not less than or not more than the predetermined threshold.

In some embodiments, provided is a non-transitory computer-readable recording medium with an executable program for an ultrasound observation apparatus stored thereon. The ultrasound observation apparatus has an ultrasound probe configured to transmit a first ultrasound signal and a second ultrasound signal to a specimen along a same line, and to receive first and second ultrasound echo signals generated by reflection of the first and second ultrasound signals from the specimen, the second ultrasound signal having a different phase or amplitude from the first ultrasound signal. The program instructs the ultrasound observation apparatus to execute: by a first image data generation unit, performing a calculation process on first and second received signals, which respectively correspond to the first and second ultrasound echo signals, to compute a third received signal, and generating image data of a first ultrasound image having a predetermined display mode, using the third received signal; by a feature extraction unit: calculating a first feature based on a frequency spectrum of the first ultrasound echo signal; calculating a second feature based on a frequency spectrum of the second ultrasound echo signal; and extracting a third feature from the calculated first and second features so as to be associated with a pixel position in the first ultrasound image; generating, by a second image data generation unit, image data of a second ultrasound image having a second display mode different from the predetermined display mode, at a pixel position where the third feature is not less than or not more than a predetermined threshold; and generating, by an image composition unit, image data of a composite image by combining the first ultrasound image with the second ultrasound image at the pixel position where the third feature is not less than or not more than the predetermined threshold.

The above and other features, advantages and technical and industrial significance of this invention will be better understood by reading the following detailed description of presently preferred embodiments of the invention, when considered in connection with the accompanying drawings.

DETAILED DESCRIPTION

Embodiments of an ultrasound observation apparatus, a method of operating an ultrasound observation apparatus, and an operating program for an ultrasound observation apparatus according to the present invention will be described in detail below with reference to the drawings. Note that the present invention is not limited to these embodiments. The same reference signs are used to designate the same elements throughout the drawings.

First Embodiment

Figure 1:
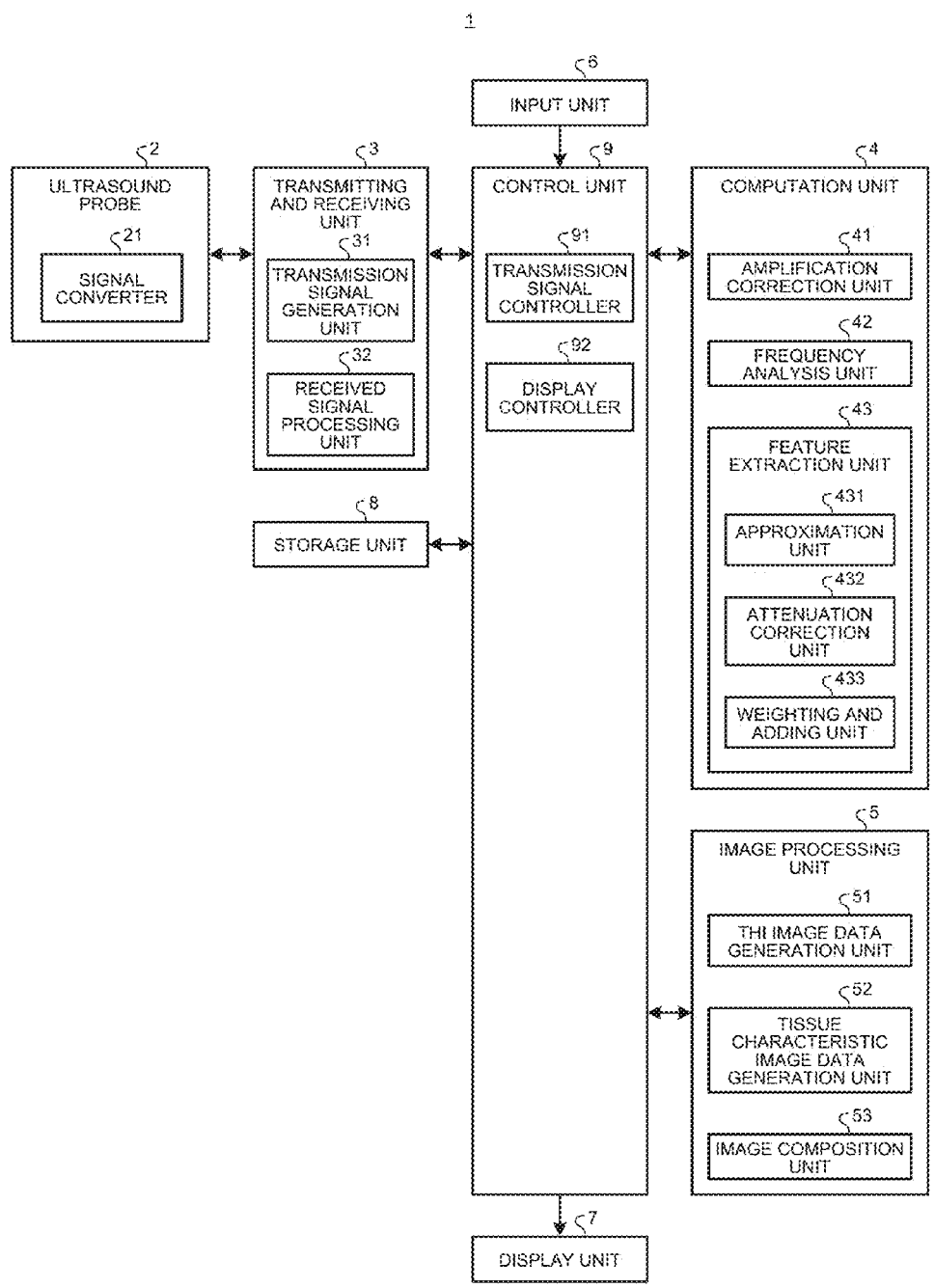
FIG. 1 is a block diagram illustrating an exemplary configuration of an ultrasound observation apparatus according to a first embodiment of the present invention.

FIG. 1 is a block diagram illustrating an exemplary configuration of an ultrasound observation apparatus according to a first embodiment of the present invention. An ultrasound observation apparatus 1 illustrated in the drawing is an apparatus that observes a specimen using ultrasound.

The ultrasound observation apparatus 1 includes an ultrasound probe 2 that outputs ultrasound pulses externally and receives ultrasound echoes reflected externally; a transmitting and receiving unit 3 that performs transmission and reception of electrical signals with the ultrasound probe 2; a computation unit 4 that performs a predetermined calculation process on electrical echo signals into which ultrasound echoes are converted; an image processing unit 5 that performs generation of image data corresponding to the electrical echo signals into which the ultrasound echoes are converted; an input unit 6 that accepts input of various types of information to the ultrasound observation apparatus 1; a display unit 7 that is implemented using a display panel including liquid crystal, organic EL, or the like, and that displays various types of information including an image generated by the image processing unit 5; a storage unit 8 that stores parameters used in the calculation process and image processing for the echo signals and various types of information such as results of these processes; and a control unit 9 that performs operational control of the ultrasound observation apparatus 1.

The ultrasound probe 2 includes a signal converter 21 including a plurality of ultrasound transducers that convert an electrical pulse signal received from the transmitting and receiving unit 3 into ultrasound pulses (ultrasound signal) and transmit the ultrasound pulses, and receive an ultrasound echo reflected from a specimen and convert the ultrasound echo into an electrical echo signal. The type of the ultrasound probe 2 is not particularly limited and may be of an external type (a linear type, a sector type, a convex type, etc.) which is used outside the body such as the abdomen or the chest, or may be an ultrasound endoscope which is inserted into the body and used. In addition, a scanning method for the ultrasound probe 2 may be a mechanical scanning method that controls the direction of ultrasound transmission by mechanical control performed on the ultrasound transducers, or may be an electronic scanning method that controls the direction of ultrasound transmission by electronic control performed on the plurality of ultrasound transducers. Furthermore, a 2D array that can acquire three-dimensional image information may be used.

The transmitting and receiving unit 3 is electrically connected to the ultrasound probe 2, and transmits an electrical pulse signal to the ultrasound probe 2 and receives an electrical echo signal from the ultrasound probe 2. More specifically, the transmitting and receiving unit 3 includes a transmission signal generation unit 31 and a received signal processing unit 32. Note that when the ultrasound probe 2 employs the electronic scanning method, the transmitting and receiving unit 3 includes a multichannel circuit for combining beams which is provided for the plurality of ultrasound transducers.

The transmission signal generation unit 31 generates a pulse signal having a predetermined waveform under control of the control unit 9, and performs processes, such as amplification and transmission delay for transmitting ultrasound in a desired direction, on the pulse signal and transmits the processed pulse signal to the ultrasound probe 2.

The received signal processing unit 32 performs predetermined signal processing, such as amplification, filtering, A/D conversion, and delay addition, on an electrical echo signal received from the ultrasound probe 2, and thereby generates and outputs a digital received signal (digital RF signal) for each line corresponding to a direction of ultrasound transmission.

Figure 2:
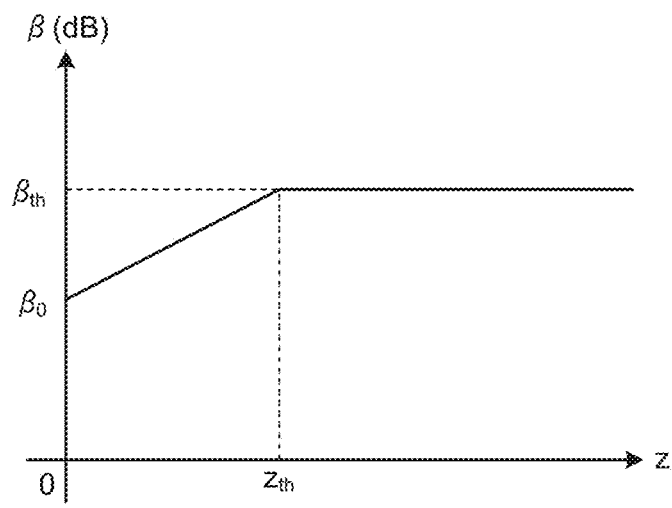
FIG. 2 is a diagram illustrating a relationship between amplification factor and reception depth for an amplification process (STC correction) performed by a received signal processing unit illustrated in FIG. 1.

More specifically, the received signal processing unit 32 performs, as an amplification process, STC (Sensitivity Time Control) correction where an echo signal with a larger reception depth is amplified with a higher amplification factor. FIG. 2 is a diagram illustrating a relationship between reception depth and amplification factor for an amplification process performed by the received signal processing unit 32. A reception depth z illustrated in FIG. 2 is an amount computed based on the elapsed time from a time point when reception of ultrasound is started. As illustrated in FIG. 2, when the reception depth z is smaller than a threshold $z_{th}$, an amplification factor $\beta$ (dB) increases linearly from $\beta_0$ to $\beta_{th}$ ($>\beta_0$) along with an increase in the reception depth z. In addition, when the reception depth z is greater than or equal to the threshold $z_{th}$, the amplification factor $\beta$ takes a constant value $\beta_{th}$. The value of the threshold $z_{th}$ is a value at which almost all of an ultrasound signal received from a specimen is attenuated and thus noise is dominant. More generally, when the reception depth z is smaller than the threshold $z_{th}$, the amplification factor $\beta$ monotonously increases along with an increase in the reception depth z.

In addition, a received digital signal for each line (sound ray) corresponding to a direction of ultrasound transmission, which is output from the received signal processing unit 32 is hereinafter also referred to as sound ray data.

The computation unit 4 includes an amplification correction unit 41 that performs amplification correction where the amplification factor is constant irrespective of the reception depth, on a received signal which is output from the transmitting and receiving unit 3; a frequency analysis unit 42 that performs frequency analysis of an echo signal by performing a fast Fourier transform (FFT) on the received signal having been subjected to the amplification correction; and a feature extraction unit 43 that extracts feature from frequency spectra (power spectra) which are computed by the frequency analysis unit 42, so as to be associated with pixel positions in an image.

Figure 3:
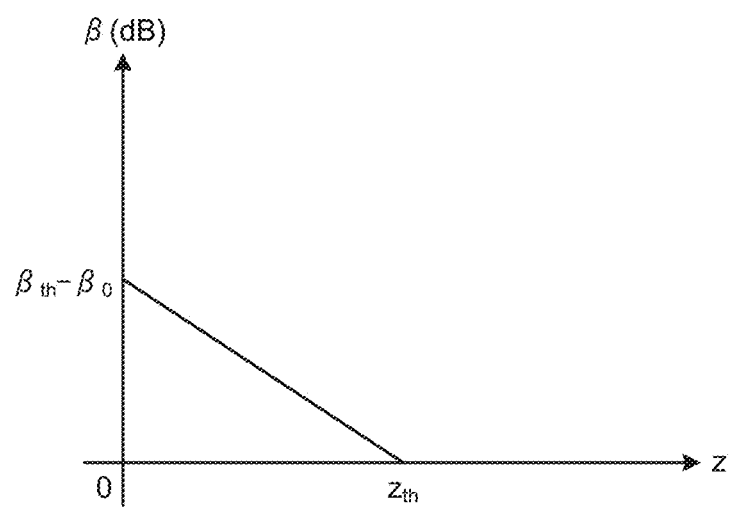
FIG. 3 is a diagram illustrating a relationship between reception depth and amplification factor for an amplification correction process performed by an amplification correction unit illustrated in FIG. 1.

FIG. 3 is a diagram illustrating a relationship between reception depth and amplification factor for an amplification correction process performed by the amplification correction unit 41. As illustrated in FIG. 3, an amplification factor $\beta$ (dB) for the amplification correction process performed by the amplification correction unit 41 takes a maximum value $\beta_{th}-\beta_0$ when a reception depth z is zero, and decreases linearly until the reception depth z reaches a threshold $z_{th}$ from zero, and is zero when the reception depth z is greater than or equal to the threshold $z_{th}$. By the amplification correction unit 41 performing amplification correction on a received signal using the amplification factor as defined above, the influence of STC correction performed by the received signal processing unit 32 is cancelled out, thereby enabling to output a signal with a constant amplification factor $\beta_{th}$. Note that the relationship between reception depth z and the amplification factor $\beta$ for the amplification correction process performed by the amplification correction unit 41, of course, varies depending on the relationship between reception depth and amplification factor for the received signal processing unit 32.

Here, the STC correction performed by the received signal processing unit 32 is correction to uniformly amplify the amplitude of an analog signal waveform over the entire frequency band. Hence, as will be described later, when a THI (tissue harmonic imaging) image that uses the amplitude of ultrasound is generated, sufficient effect can be obtained by performing STC correction, whereas when an ultrasound frequency spectrum is computed, the influence of attenuation associated with propagation of ultrasound cannot be accurately eliminated. To solve this problem, it is considered that when a THI image is generated, received signals having been subjected to STC correction are output; on the other hand, when an image based on frequency spectra is generated, another transmission different from transmission for creating a THI image is performed and received signals having not been subjected to STC correction are output. However, in this case, there is a problem that the frame rate of image data generated based on received signals decreases. Hence, by providing the amplification correction unit 41 at the previous stage to the frequency analysis unit 42, while the frame rate of image data to be generated is maintained, the influence of STC correction can be eliminated once for signals having been subjected to STC correction for a THI image.

The frequency analysis unit 42 performs, for received signals output from the transmitting and receiving unit 3, a fast Fourier transform on FFT data groups each having a predetermined amount of data, and thereby computes frequency spectra for a plurality of locations (data positions) on sound rays. In general, a frequency spectrum shows different tendencies depending on the tissue characteristic of a specimen. This is because the frequency spectrum has a correlation with the size, density, acoustic impedance, etc., of a specimen serving as a scatterer that scatters ultrasound. Note that in the first embodiment the "tissue characteristic" refers to a condition of tissue, e.g., cancer, an endocrine tumor, a mucinous tumor, normal tissue, or a vessel.

The feature extraction unit 43 includes an approximation unit 431 that performs an approximation process on the frequency spectra computed by the frequency analysis unit 42, and thereby computes pre-correction feature; an attenuation correction unit 432 that performs an attenuation correction process, which reduces contribution of attenuation occurring according to the reception depth and frequency of ultrasound when the ultrasound is propagated, on the pre-correction feature computed by the approximation unit 431; and a weighting and adding unit 433 that calculates a weighted sum of the features having been subjected to the attenuation correction process.

The approximation unit 431 approximates a frequency spectrum by regression analysis using a linear expression (regression line), and thereby extracts pre-correction feature that characterizes the approximated linear expression. Specifically, the approximation unit 431 extracts, as pre-correction feature, the slope $a_0$ and intercept $b_0$ of a linear expression by regression analysis. Note that the approximation unit 431 may compute the intensity (also referred to as Mid-band fit) $c_0 = a_0 f_M + b_0$ of a center frequency $f_M = (f_L + f_H)/2$ of a frequency band ($f_L < f < f_H$), as pre-correction feature other than the slope $a_0$ and the intercept $b_0$.

Of the three pre-correction feature, the slope $a_0$ has a correlation with the size of an ultrasound scatterer, and in general, it is considered that the larger the scatterer the smaller the value of the slope. In addition, the intercept $b_0$ has a correlation with the size of the scatterer, the difference in acoustic impedance, the density (concentration) of the scatterer, etc. Specifically, it is considered that the larger the scatterer the larger the value of the intercept $b_0$, the larger the difference in acoustic impedance the larger the value of the intercept $b_0$, and the higher the density (concentration) of the scatterer the larger the value of the intercept $b_0$. The intensity of the center frequency $f_M$ (hereinafter, simply referred to as "intensity") $c_0$ is an indirect parameter derived from the slope $a_0$ and the intercept $b_0$, and provides spectral intensity at the center of an effective frequency band. Hence, it is considered that the intensity $c_0$ has a certain degree of correlation with the luminance of a THI image or the like which is generated based on the amplitudes of received signals, in addition to the size of the scatterer, the difference in acoustic impedance, and the density of the scatterer. Note that an approximate polynomial computed by the approximation unit 431 is not limited to a linear expression, and it is also possible to use quadratic or higher-order approximate polynomials.

The attenuation correction unit 432 performs an attenuation correction process, which reduces contribution of attenuation occurring according to the reception depth and frequency of ultrasound when the ultrasound is propagated, on the pre-correction feature extracted by the approximation unit 431.

In general, the amount of attenuation of ultrasound $A(f, z)$ is represented by:

$$A(f,z) = 2\alpha z f \quad (1)$$

where $\alpha$ is the attenuation factor, $z$ is the reception depth of ultrasound, and $f$ is the frequency. As is also clear from equation (1), the amount of attenuation $A(f, z)$ is proportional to the frequency $f$. When an observation target is a living body, a specific value of the attenuation factor $\alpha$ is 0.0 to 1.0 (dB/cm/MHz), more preferably, 0.3 to 0.7 (dB/cm/MHz), and is determined according to the region of the living body. For example, when the observation target is the pancreas, the attenuation factor $\alpha$ may be determined such that $\alpha = 0.6$ (dB/cm/MHz). Note that in the first embodiment it may be configured such that the value of the attenuation factor $\alpha$ is settable or changeable by input from the input unit 6.

The attenuation correction unit 432 performs attenuation correction on pre-correction feature (slope $a_0$, intercept $b_0$, and intensity $c_0$) which is acquired by the approximation process, in the following manner and thereby extracts feature:

$$a = a_0 + 2\alpha z \quad (2)$$

$$b = b_0 \quad (3)$$

$$c = c_0 + 2\alpha z f_M (= a f_M + b) \quad (4)$$

As is also clear from (2) and (4), the attenuation correction unit 432 performs correction where the larger the reception depth $z$ of ultrasound the larger the amount of correction. In addition, according to equation (3), correction for the intercept is identify transformation. This is because the intercept is a frequency component for a frequency of 0 (Hz) and thus is not subjected to the influence of attenuation.

A straight line corresponding to corrected feature is represented by the following equation:

$$I = af + b = (a_0 + 2\alpha z)f + b_0 \quad (5)$$

As is also clear from this equation (5), the straight line corresponding to the corrected feature has a large slope and an identical intercept, compared to a straight line corresponding to pre-correction feature.

The weighting and adding unit 433 calculates the weighted sum of the features that are respectively extracted from sound ray data corresponding to two ultrasound echo signals which are generated by transmitting two ultrasound signals toward a specimen at different points in time along the same line and by reflection of the two ultrasound signals from the specimen.

The image processing unit 5 includes a THI image data generation unit (image data generation unit) 51 that generates image data of a THI image (ultrasound image), based on harmonic components of sound ray data; a tissue characteristic image data generation unit (second image data generation unit) 52 that generates image data of a tissue characteristic image (second ultrasound image) representing the tissue characteristics of body tissue, based on feature extracted by the feature extraction unit 43; and an image composition unit 53 that generates image data of a composite image where the THI image and the tissue characteristic image are combined.

The THI image data generation unit 51 extracts harmonic components from received signals corresponding to echoes of ultrasound signals (ultrasound echoes), respectively, which are sequentially transmitted to a specimen along the same line and which have the same waveform and different amplitudes or phases; and generates THI image data based on the extracted harmonic components.

Figure 4:
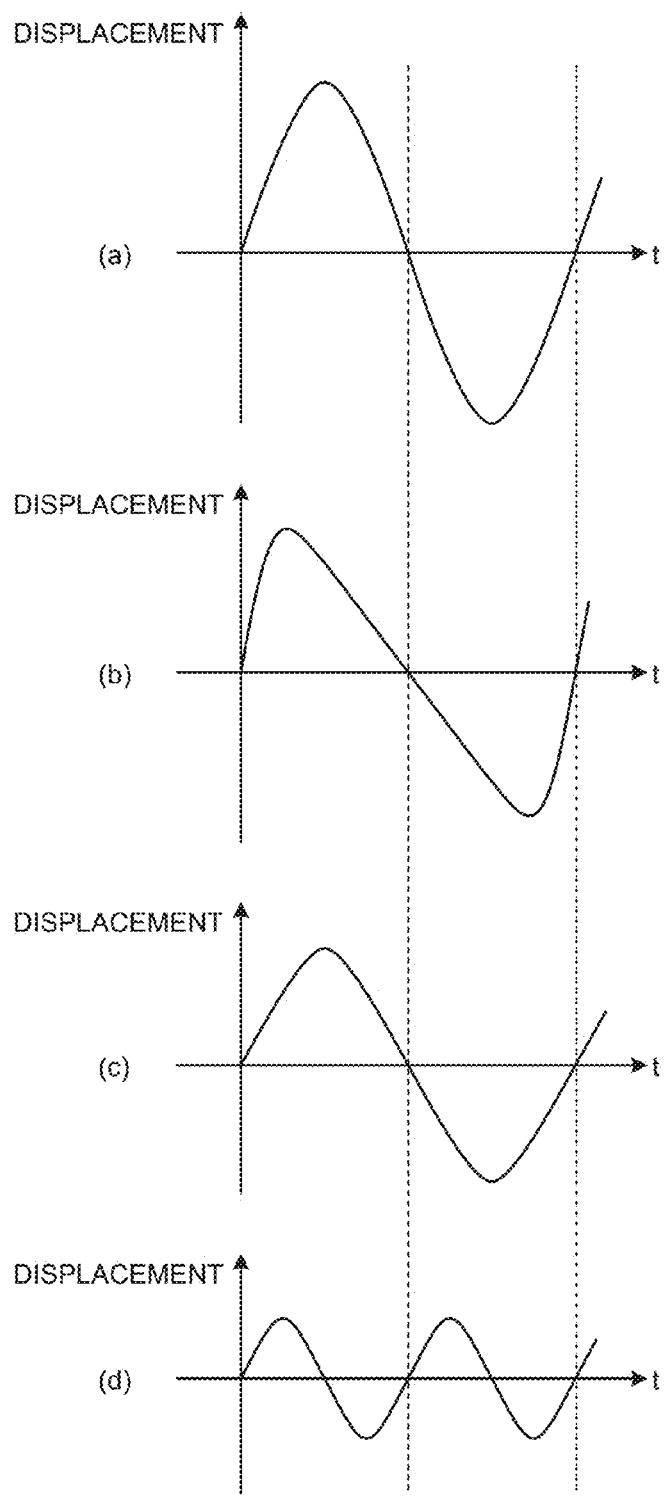
FIG. 4 is a schematic diagram illustrating examples of waveforms of a first ultrasound signal and an ultrasound echo signal thereof.
Figure 5:
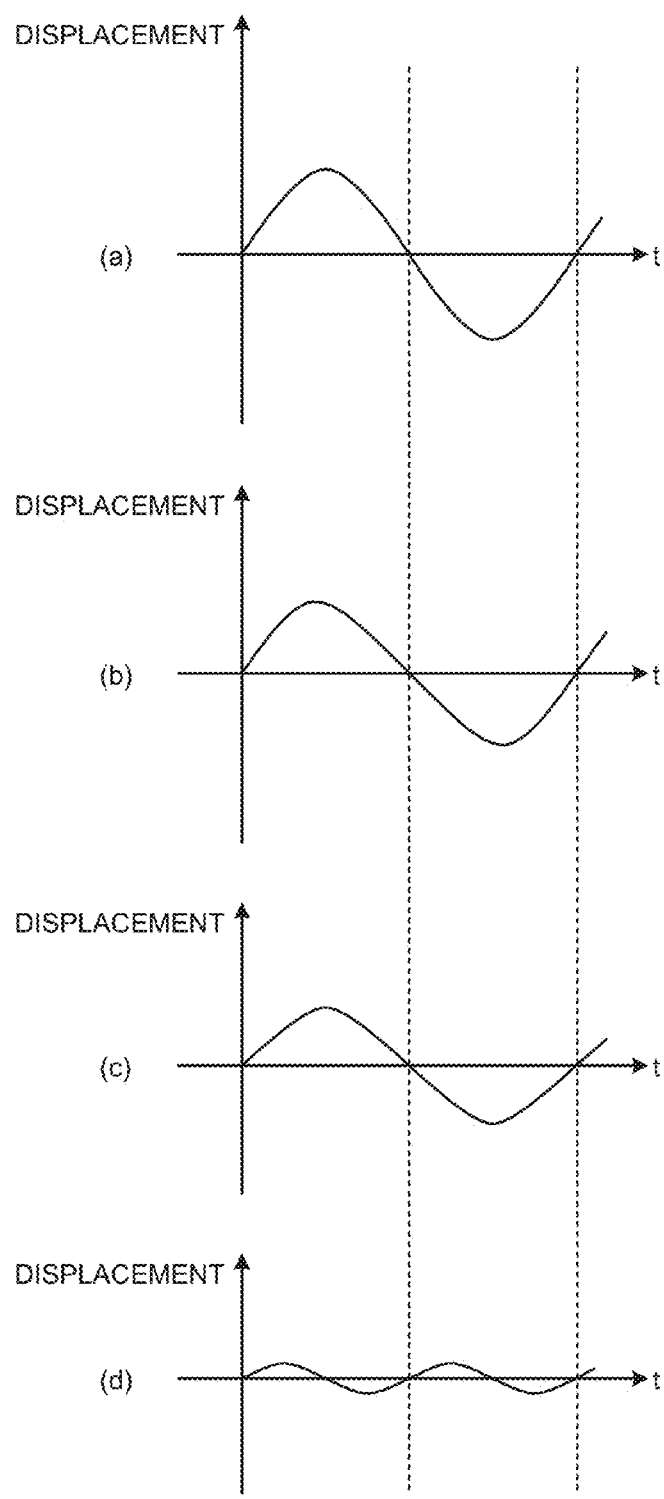
FIG. 5 is a schematic diagram illustrating examples of waveforms of a second ultrasound signal and an ultrasound echo signal thereof.

Now, the principle of THI will be described with reference to FIGS. 4 and 5. FIGS. 4 and 5 are schematic diagrams illustrating examples of waveforms of transmitted ultrasound signals and ultrasound echo signals thereof. Here, the case of transmitting two ultrasound signals having the same waveform and the same phase and different amplitudes will be described.

It is known that, when ultrasound is propagated through body tissue, a nonlinear effect occurs more strongly for larger amplitude of ultrasound. For example, when a first ultrasound signal having a waveform illustrated in (a) of FIG. 4 is transmitted, due to the nonlinear effect of body tissue, as illustrated in (b) of FIG. 4, distortion occurs in the waveform of a first ultrasound echo signal generated by reflection of the first ultrasound signal by a specimen. The first ultrasound echo signal can be represented as a combined wave of a fundamental wave component illustrated in (c) of FIG. 4, a second harmonic component illustrated in (d) of FIG. 4, and furthermore, a third or higher harmonic component.

On the other hand, when, as illustrated in (a) of FIG. 5, a second ultrasound signal having the same phase as the first ultrasound signal and a smaller amplitude than the first ultrasound signal is transmitted, the nonlinear effect of body tissue is smaller than that for the case of the first ultrasound signal. Hence, in a second ultrasound echo signal generated by reflection of the second ultrasound signal by the specimen, as illustrated in (b) of FIG. 5, waveform distortion is smaller compared to that in (b) of FIG. 4. The second ultrasound echo signal can be represented as a combined wave of a fundamental wave component illustrated in (c) of FIG. 5, a second harmonic component illustrated in (d) of FIG. 5, and furthermore, a third or higher harmonic component.

Here, the amplitude of the fundamental wave component has a value nearly proportional to the transmitted ultrasound signal. On the other hand, the amplitude of the harmonic component has a value nearly proportional to the square of the amplitude of the fundamental wave component. Hence, when the amplitude of the second ultrasound signal is a factor of $1/n$ smaller than that of the first ultrasound signal ($n>0$ and $n \ne 1$, $n=2$ in FIGS. 4 and 5), the amplitude of the second harmonic component of the second ultrasound echo signal (see (d) of FIG. 5) becomes $1/n^2$ (1/4 in FIGS. 4 and 5) of the amplitude of the second harmonic component of the first ultrasound echo signal (see (d) of FIG. 4). Hence, by multiplying the second ultrasound echo signal by a factor of n and subtracting the resulting second ultrasound echo signal from the first ultrasound echo signal, the fundamental wave component is cancelled out, enabling to extract the second harmonic component.

The THI image data generation unit 51 extracts second harmonic components from sound ray data output from the transmitting and receiving unit 3, according to the above-described principle of THI, and further performs predetermined processes, such as a bandpass filtering process, a detection process, and a logarithmic compression process, on the second harmonic components, and thereby generates THI image data. A display mode of a THI image represented by the THI image data is grayscale display including two- or three-dimensional image space where the values of R (red), G (green), and B (blue), which are variables when an RGB color system is adopted as a color space, match each other.

The tissue characteristic image data generation unit 52 generates tissue characteristic image data representing the tissue characteristics of a specimen, based on the feature extracted by the feature extraction unit 43. More specifically, the tissue characteristic image data generation unit 52 assigns a pixel whose feature is smaller than a predetermined threshold, with a pixel value of a color according to the feature; on the other hand, the tissue characteristic image data generation unit 52 assigns a pixel whose feature is greater than or equal to the predetermined threshold, with zero (i.e., black) as a pixel value. Namely, a display mode (second display mode) of the tissue characteristic image is color display. Alternatively, reversely, a pixel whose feature is larger than the predetermined threshold may be assigned a pixel value of a color according to the feature, and on the other hand, a pixel whose feature is less than or equal to the predetermined threshold may be assigned zero as a pixel value.

The image composition unit 53 generates, using the THI image data generated by the THI image data generation unit 51, image data of a composite image where areas that are specified based on the feature extracted by the feature extraction unit 43 are displayed in a different mode than the display mode of the THI image. In the first embodiment, the image composition unit 53 generates composite image data of a composite image where a THI image and a tissue characteristic image are combined, using the THI image data generated by the THI image data generation unit 51 and the tissue characteristic image data generated by the tissue characteristic image data generation unit 52. The composite image displayed using the composite image data is an image where the color tissue characteristic image is superimposed on the grayscale THI image.

The input unit 6 is implemented using interfaces such as a keyboard, a mouse, a touch panel, and a card reader, and inputs to the control unit 9 a signal generated according to an operation performed externally by an operator, etc. Specifically, the input unit 6 accepts patient identification information for identifying a patient to be examined, an instruction to set an area of interest, instructions to start various types of operation, etc., and inputs signals representing these information and instructions to the control unit 9. The area of interest as used herein refers to an area in the THI image displayed on the display unit 7 that is specified by the operator of the ultrasound observation apparatus 1 using the input unit 6.

The storage unit 8 is implemented using, for example, a ROM that pre-stores an operating program for the ultrasound observation apparatus 1 according to the first embodiment, a program for starting up a predetermined OS, etc., and a RAM that stores parameters and data used in processes, etc. More specifically, the storage unit 8 stores sound ray data output from the transmitting and receiving unit 3, window functions (Hamming, Hanning, Blackman, etc.) used by the frequency analysis unit 42, feature extracted by the feature extraction unit 43, THI image data, tissue characteristic image data, and composite image data which are generated by the image processing unit 5, etc.

The control unit 9 includes a transmission signal controller 91 that controls pulse signal generation operation of the transmission signal generation unit 31; and a display controller 92 that controls display operation of the display unit 7. The transmission signal controller 91 controls the transmission signal generation unit 31 such that transmission operation where a plurality of ultrasound signals having the same waveform and different phases or amplitudes are sequentially transmitted along the same line traveling toward a specimen is considered one set, and a specimen is scanned by ultrasound which is transmitted and received by this one set of transmission operation.

Elements of the ultrasound observation apparatus 1 having the above-described functional configuration other than the ultrasound probe 2 are implemented using a computer that includes a CPU having calculation and control functions. The CPU included in the ultrasound observation apparatus 1 performs a calculation process related to a method of operating the ultrasound observation apparatus 1 according to the first embodiment, by reading from the storage unit 8 information and various types of programs including the above-described operating program for the ultrasound observation apparatus 1, which are stored and retained in the storage unit 8.

Note that the operating program for the ultrasound observation apparatus 1 according to the first embodiment can also be widely distributed by recording the operating program in a computer-readable recording medium such as a hard disk, a flash memory, a CD-ROM, a DVD-ROM, or a flexible disk.

Figure 6:
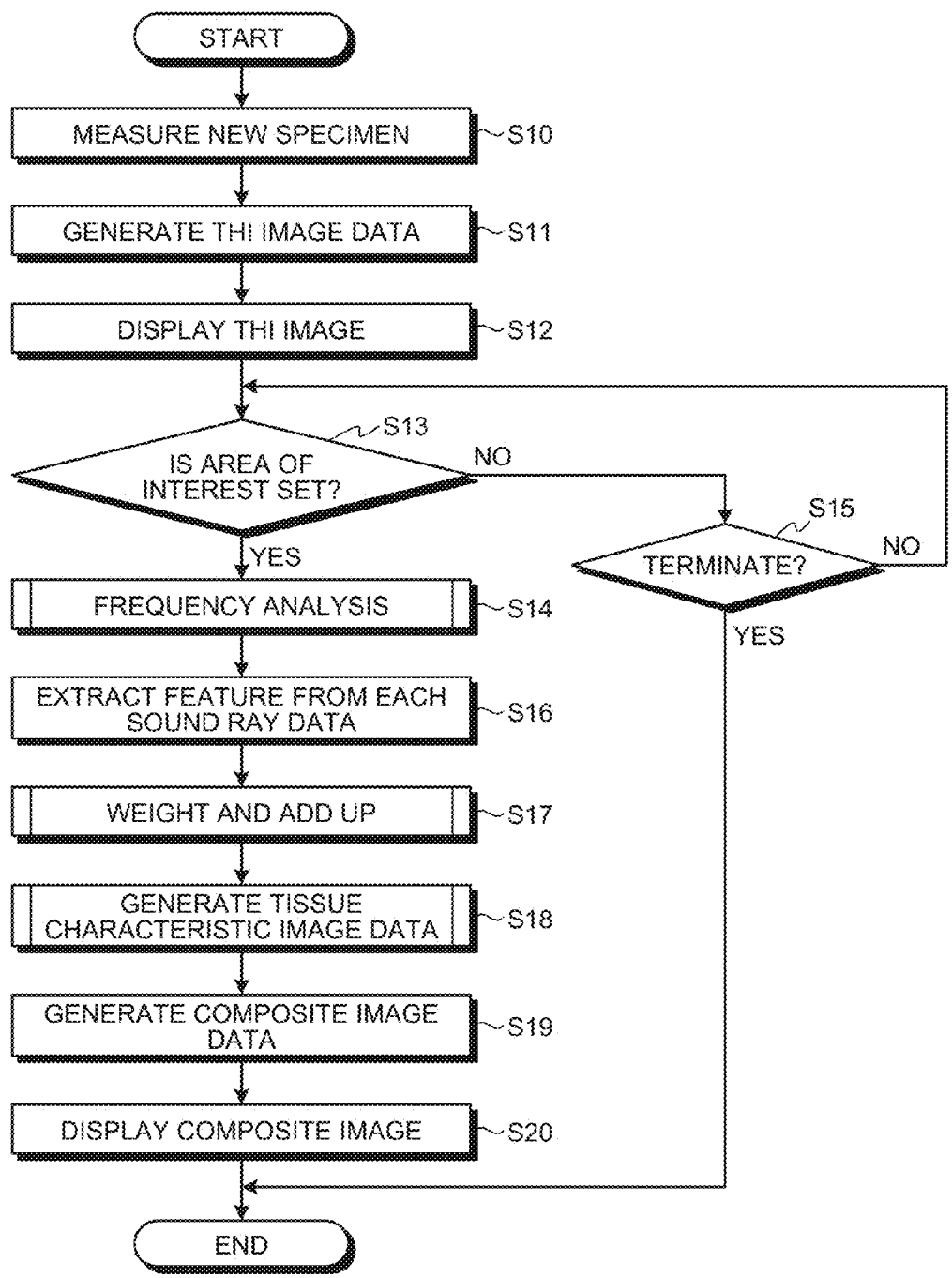
FIG. 6 is a flowchart illustrating the operation of the ultrasound observation apparatus illustrated in FIG. 1.

Next, the operation of the ultrasound observation apparatus 1 will be described. FIG. 6 is a flowchart illustrating the operation of the ultrasound observation apparatus 1.

First, at step S10, the ultrasound observation apparatus 1 measures a new specimen by the ultrasound probe 2. Specifically, in the first embodiment, the ultrasound observation apparatus 1 sequentially transmits first and second ultrasound signals having the same waveform and the same phase and different amplitudes along the same line traveling toward a specimen, and receives first and second ultrasound echo signals generated by reflection of the first and second ultrasound signals by the specimen. At this time, a frequency band of the first and second ultrasound signals may be a wide band that covers substantially the entire frequency band of the ultrasound transducers. By that, an accurate linear approximation is possible in a process of extracting feature from frequency spectra which will be described later.

The ultrasound echo signals received by the ultrasound probe 2 are converted into electrical echo signals, and furthermore, the electrical echo signals are subjected to predetermined signal processing such as amplification (STC correction), filtering, A/D conversion, and delay addition, in the received signal processing unit 32. By that, first and second sound ray data (received signals) are generated for each line along which the first and second ultrasound signals are transmitted. Namely, two types of sound ray data are acquired for one line. The ultrasound observation apparatus 1 repeatedly performs such ultrasound transmission/reception and signal processing while moving the line along which ultrasound signals are transmitted.

At subsequent step S11, the THI image data generation unit 51 generates THI image data, based on the first and second sound ray data which are acquired at step S10. For example, as illustrated in (a) of FIG. 4 and (a) of FIG. 5, when the amplitude of the second ultrasound signal is 1/n of the amplitude of the first ultrasound signal (e.g., n=2), the THI image data generation unit 51 multiplies a data value (corresponding to amplitude) of the second sound ray data (second received signal) by a factor of n, and then subtracts the resulting second sound ray data from the first sound ray data (first received signal), and thereby generates third sound ray data (third received signal) corresponding to a second harmonic component. Then, predetermined processes such as a bandpass filtering process, a detection process, and a logarithmic compression process are performed on the third sound ray data, by which THI image data is generated.

Figure 7:
FIG. 7 is a diagram illustrating exemplary display of a THI image.

At step S12, the display controller 92 displays a THI image based on the THI image data generated by the THI image data generation unit 51. FIG. 7 is a diagram illustrating exemplary display of the THI image. As described above, the THI image is a grayscale image where the values of R (red), G (green), and B (blue) of each pixel match each other.

Thereafter, if an area of interest is set through the input unit 6 (step S13: Yes), the computation unit 4 captures the first and second sound ray data acquired at step S10, performs amplification correction on these sound ray data, and then performs frequency analysis by FFT computation, and thereby computes frequency spectra (step S14). At this step S13, it is also possible to set the entire area of the image as an area of interest. On the other hand, if an area of interest is not set (step S13: No) and if an instruction to terminate the operation is input through the input unit 6 (step S15: Yes), the ultrasound observation apparatus 1 terminates its operation. In contrast to this, if an area of interest is not set (step S13: No) and if an instruction to terminate the operation is not input through the input unit 6 (step S15: No), the operation of the ultrasound observation apparatus 1 returns to step S13.

Figure 8:
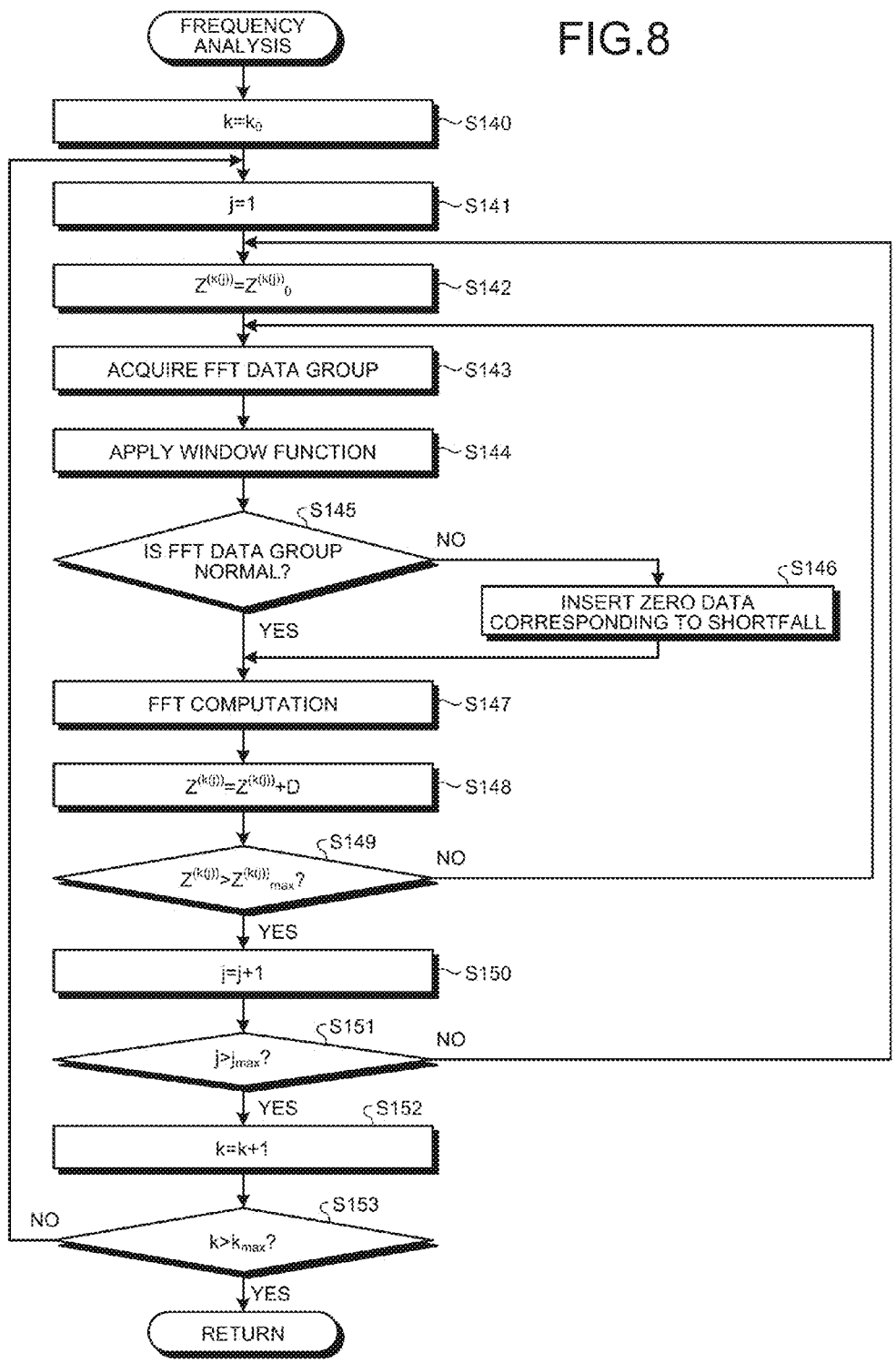
FIG. 8 is a flowchart illustrating a frequency analysis process performed by a frequency analysis unit illustrated in FIG. 1.

FIG. 8 is a flowchart illustrating the frequency analysis process performed by the frequency analysis unit 42 at step S14.

First, at step S140, the frequency analysis unit 42 sets a counter k for identifying a line for sound ray data to be analyzed to $k_0$. At subsequent step S141, the frequency analysis unit 42 sets a counter j for identifying sound ray data to be analyzed to 1.

Figure 9:
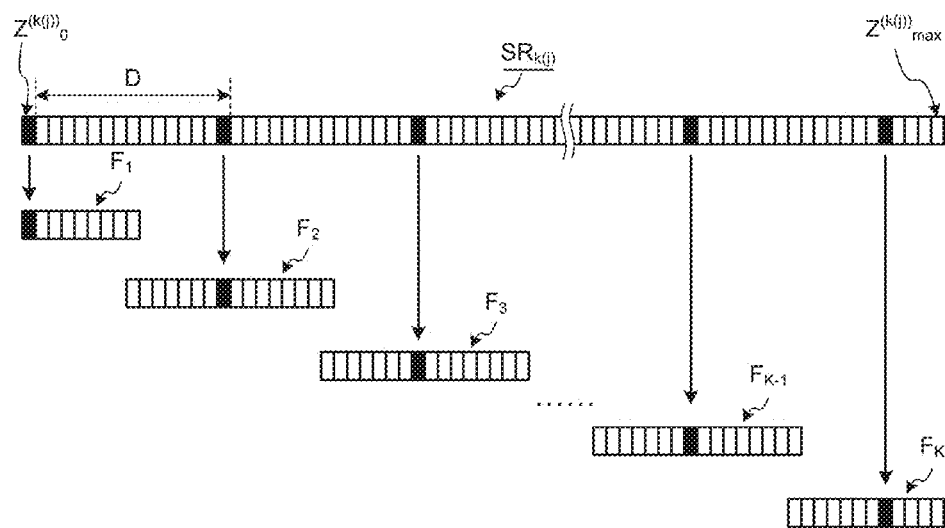
FIG. 9 is a diagram schematically illustrating a data array of one sound ray.

At subsequent step S142, the frequency analysis unit 42 sets an initial value $Z^{(k(j))}_0$ of a data position (corresponding to reception depth) $Z^{(k(j))}$ that represents a data group (FFT data group) acquired for FFT computation. FIG. 9 is a diagram schematically illustrating a data array of one sound ray. In sound ray data $SR_{k(j)}$ illustrated in the drawing, a white or black rectangle indicates one piece of data. The sound ray data $SR_{k(j)}$ is discretized in time intervals corresponding to the sampling frequency (e.g., 50 MHz) of A/D conversion performed by the received signal processing unit 32. Although FIG. 9 illustrates the case in which the first data position of the sound ray data $SR_{k(j)}$ is set as the initial value $Z^{(k(j))}_0$, the position of the initial value can be set arbitrarily.

At subsequent step S143, the frequency analysis unit 42 acquires an FFT data group for the data position $Z^{(k(j))}$. Then, at step S144, a window function stored in the storage unit 8 is applied to the acquired FFT data group. By thus allowing the window function to act on the FFT data group, the FFT data group is avoided from becoming discontinuous at boundaries, enabling to prevent the occurrence of artifacts.

At subsequent step S145, the frequency analysis unit 42 determines whether the FFT data group for the data position $Z^{(k(j))}$ is a normal data group. Here, the FFT data group needs to have a power-of-two number of data. In the following, the number of data included in an FFT data group is $2^n$ (n is a positive integer). The FFT data group being normal refers to that the data position $Z^{(k(j))}$ is a $2^{n-1}$th position from the top of the FFT data group. In other words, the FFT data group being normal refers to that there are $2^{n-1}-1$ (=N) pieces of data before the data position $Z^{(k(j))}$ and there are $2^{n-1}$ (=M) pieces of data after the data position $Z^{(k(j))}$. In the case illustrated in FIG. 9, FFT data groups $F_2$ and $F_3$ are both normal. Note that FIG. 9 exemplifies the case of n=4 (N=7 and M=8).

If, as a result of the determination at step S145, the FFT data group for the data position $Z^{(k(j))}$ is normal (step S145: Yes), processing of the frequency analysis unit 42 transitions to step S147 which will be described later.

On the other hand, if, as a result of the determination at step S145, the FFT data group for the data position $Z^{(k(j))}$ is not normal (step S145: No), the frequency analysis unit 42 inserts zero data corresponding to a shortfall and thereby generates a normal FFT data group (step S146). The FFT data group that is determined at step S145 to be not normal is acted on by the window function before adding zero data. Hence, even if zero data is inserted into the FFT data group, discontinuity of data does not occur. After step S146, processing of the frequency analysis unit 42 transitions to step S147 which will be described later.

Figure 10:
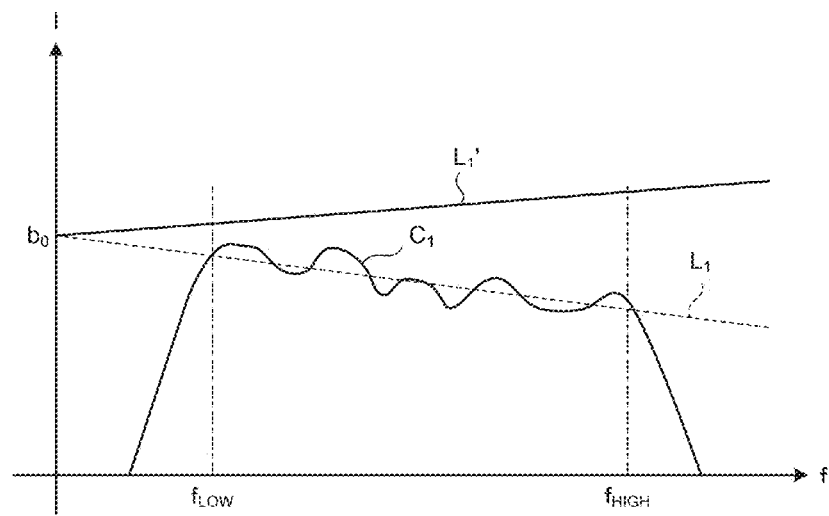
FIG. 10 is a diagram illustrating an example of a frequency spectrum computed by the frequency analysis unit illustrated in FIG. 1.

At step S147, the frequency analysis unit 42 performs FFT computation using the FFT data group and thereby obtains a frequency spectrum including complex numbers. As a result, for example, a spectrum $C_1$ such as that illustrated in FIG. 10 is obtained.

At subsequent step S148, the frequency analysis unit 42 changes the data position $Z^{(k(j))}$ by a step width D. It is assumed that the step width D is pre-stored in the storage unit 8. FIG. 9 exemplifies the case of D=15. It is desirable that the step width D match a data step width which is used when the THI image data generation unit 51 generates THI image data, but when the amount of calculation of the frequency analysis unit 42 needs to be reduced, a larger value than the data step width may be set.

At subsequent step S149, the frequency analysis unit 42 determines whether the data position $Z^{(k(j))}$ is greater than a maximum value $Z^{(k(j))}_{max}$ of the sound ray data $SR_{k(j)}$. If the data position $Z^{(k(j))}$ is less than or equal to the maximum value $Z^{(k(j))}_{max}$ (step S149: No), processing returns to step S143. In this manner, the frequency analysis unit 42 performs FFT computation on $[\{(Z^{(k(j))}_{max} - Z^{(k(j))}_0)/D\}+1]$ FFT data groups for the sound ray data $SR_{k(j)}$. Here, [X] represents a maximum integer not exceeding X.

On the other hand, if the data position $Z^{(k(j))}$ is greater than the maximum value $Z^{(k(j))}{}_{max}$ (step S149: Yes), then the frequency analysis unit 42 increments the counter j by 1 (step S150).

At subsequent step S151, the frequency analysis unit 42 determines whether the counter j is greater than a maximum value $j_{max}$ (step S151). Here, for the maximum value $j_{max}$, the number of sound ray data acquired for each line is set. For example, when first and second sound ray data are acquired for each line, $j_{max}=2$. If the counter j is less than or equal to the maximum value $j_{max}$ (step S151: No), processing of the frequency analysis unit 42 returns to step S142. On the other hand, if the counter j is greater than the maximum value $j_{max}$ (step S151: Yes), the frequency analysis unit 42 increments the counter k by 1 (step S152).

At subsequent step S153, the frequency analysis unit 42 determines whether the counter k is greater than a maximum value $k_{max}$. If the counter k is greater than the maximum value $k_{max}$ (step S153: Yes), the frequency analysis unit 42 ends a series of FFT processes and the operation of the ultrasound observation apparatus 1 returns to the main routine. On the other hand, if the counter k is less than or equal to the maximum value $k_{max}$ (step S153: No), processing of the frequency analysis unit 42 returns to step S141.

In this manner, the frequency analysis unit 42 performs a plurality of FFT computations for each of the first and second sound ray data which are acquired for each of ($k_{max}-k_0+1$) lines. Thereafter, the operation of the ultrasound observation apparatus 1 returns to the main routine.

Note that here the input unit 6 accepts in advance input for setting a specific area of interest and a frequency analysis process is performed only on the area of interest; however, the frequency analysis unit 42 may perform a frequency analysis process on the whole area for which ultrasound echo signals are received.

At step S16 subsequent to step S14, the feature extraction unit 43 extracts a feature from each sound ray data so as to be associated with pixel positions in a two- or three-dimensional image, based on the results of the frequency analysis at step S14. Information to be associated with each pixel position in image space is determined according to the amount of data of an FFT data group which is used when the frequency analysis unit 42 computes a frequency spectrum. Specifically, for example, a pixel position corresponding to the amount of data of one FFT data group is assigned information (feature) corresponding to feature of a frequency spectrum that is computed for the FFT data group.

In addition, at this time, when the process is performed for the second sound ray data whose amplitude is 1/n of the amplitude of the first sound ray data, the intensities of frequency spectra acquired at step S14 are multiplied by a factor of n in advance. Note that timing at which the intensities are multiplied by a factor of n may be after an attenuation correction process which will be described later.

First, the approximation unit 431 performs regression analysis on P frequency spectra which are computed by the frequency analysis unit 42, and thereby extracts pre-correction feature. Specifically, the approximation unit 431 computes, by regression analysis, a linear expression that approximates a frequency spectrum with a frequency band $f_{LOW} < f < f_{HIGH}$, and thereby extracts a slope $a_0$, an intercept $b_0$, and an intensity $c_0$ that characterize the linear expression, as pre-correction feature. A straight line $L_1$ illustrated in FIG. 10 is a pre-correction regression line obtained by this process.

Subsequently, the attenuation correction unit 432 substitutes the value of the data position $Z^{(k(j))}$ into the reception depth z in the above-described equations (2) to (4), and thereby computes a slope a, an intercept b, and an intensity c which are corrected feature. A straight line $L_1'$ illustrated in FIG. 10 is a regression line obtained at step S16.

In this manner, the approximation unit 431 and the attenuation correction unit 432 extract first and second features from the first and second sound ray data for each of pixel positions corresponding to a plurality of points on each line along which the first and second ultrasound signals are transmitted.

At subsequent step S17, the weighting and adding unit 433 calculates the weighted sum of the first and second features which are extracted for the same pixel position at step S16 to compute a third feature. Weights assigned to the first and second features both are not particularly limited as long as the weights are greater than zero. For example, when the weights assigned to the first and second features are both set to 1, the third feature which is obtained by addition of the first and second features is obtained. In addition, when the weights assigned to the first and second features are both set to 1/2, the third feature which is the average of the first and second features is obtained. Of course, the weights assigned to the first and second features may differ from each other. In addition, at this time, when a plurality of types of feature (e.g., features a, b, and c) are extracted by the approximation unit 431 and the attenuation correction unit 432, the weighting and adding unit 433 calculates the weighted sum of the features of the same type (e.g., weighted sum of features a, weighted sum of features b, and weighted sum of features c).

Figure 11:
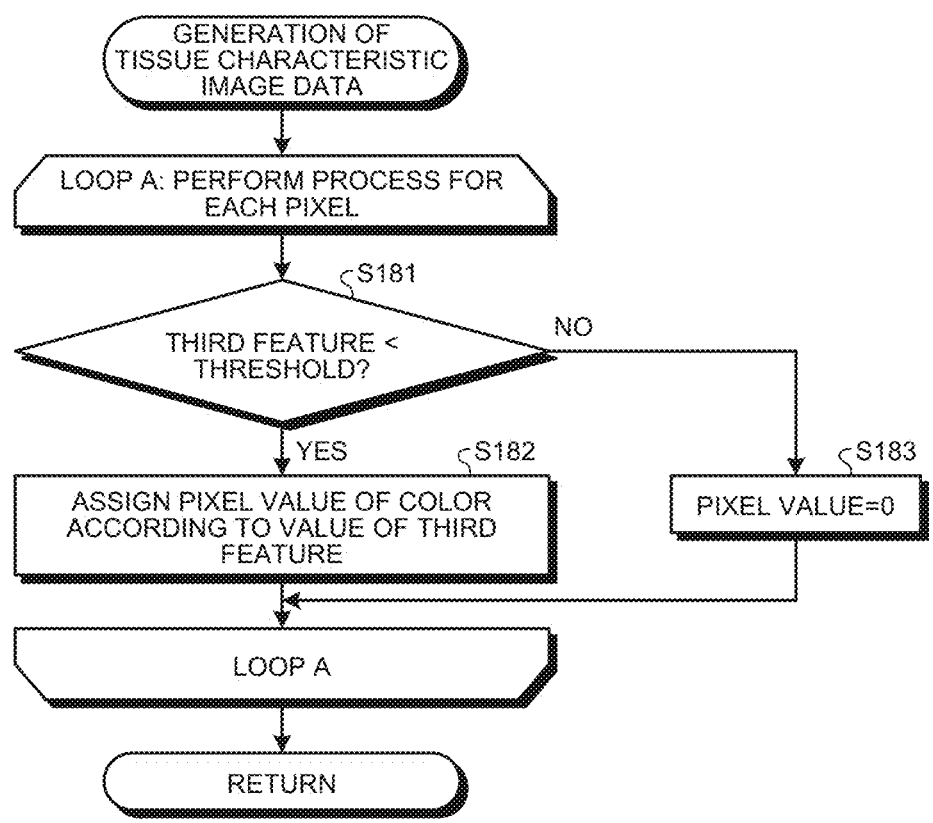
FIG. 11 is a flowchart illustrating a tissue characteristic image data generating process performed by a tissue characteristic image data generation unit illustrated in FIG. 1.

At subsequent step S18, the tissue characteristic image data generation unit 52 generates tissue characteristic image data based on the third feature computed at step S17. FIG. 11 is a flowchart illustrating a tissue characteristic image data generating process.

The tissue characteristic image data generation unit 52 performs a process of a loop A on each pixel in the area of interest. First, at step S181, the tissue characteristic image data generation unit 52 determines whether the third feature of a pixel to be processed is smaller than a predetermined threshold.

If the third feature is smaller than the predetermined threshold (step S181: Yes), the tissue characteristic image data generation unit 52 assigns the pixel with a pixel value of a color according to the value of the third feature (step S182). Specifically, the tissue characteristic image data generation unit 52 assigns each of color components R (red), G (green), and B (blue) of the pixel with a slope a, an intercept b, and an intensity c which are the third feature.

On the other hand, if the third feature assigned to the pixel to be processed is greater than or equal to the predetermined threshold (step S181: No), the tissue characteristic image data generation unit 52 assigns the pixel with zero as a pixel value (step S183). Namely, the pixel is represented in black. Thereafter, processing of the tissue characteristic image data generation unit 52 transitions to the next pixel to be processed.

Such processes are performed on all pixels in the area of interest, and then the operation of the ultrasound observation apparatus 1 returns to the main routine.

Figure 12:
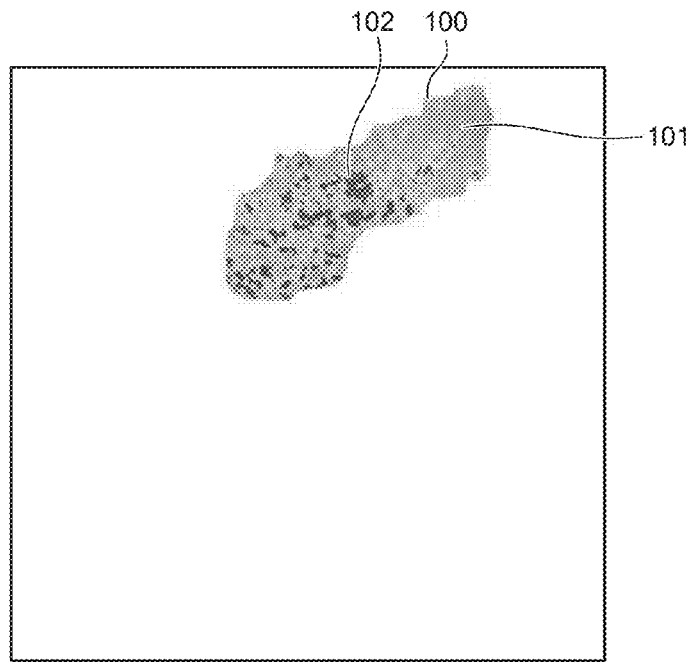
FIG. 12 is a diagram illustrating an example of a tissue characteristic image.
Figure 13:
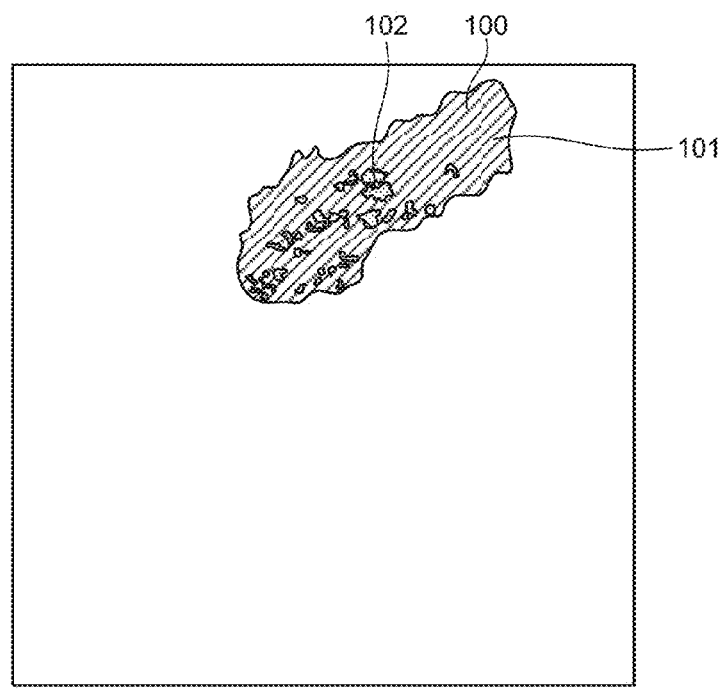
FIG. 13 is a diagram schematically illustrating the image illustrated in FIG. 12 in black and white.

FIG. 12 is a diagram illustrating an example of a tissue characteristic image generated based on the tissue characteristic image data generated at step S18. FIG. 13 is a diagram schematically illustrating the image illustrated in FIG. 12 in black and white. An area 100 illustrated in the drawings is an area whose third feature is determined at step S181 to be smaller than the predetermined threshold. The area 100 roughly includes a green-based area 101 and a red-based area 102, and a boundary portion between two areas is displayed in yellow-based color (not displayed in FIG. 13). As illustrated in FIGS. 12 and 13, each area does not include a single color. For example, the green-based area 101 is an area where pixels whose colors are close to green are gathered together. Likewise, the red-based area 102 is an area where pixels whose colors are close to red are gathered together.

At step S19 subsequent to step S18, the image composition unit 53 generates composite image data using the THI image data generated at step S11 and the tissue characteristic image data generated at step S18. More specifically, for an area in the tissue characteristic image that includes pixels with pixel values other than zero, a pixel value in the composite image is obtained by calculating the weighted sum of pixel values of pixels of the THI image and the tissue characteristic image at corresponding positions. Specifically, a pixel value (values of color components R (red), G (green), and B (blue)) of each pixel in a composite image is computed by the following equation (6):

$$g_{syn}(x,y) = w \cdot g_{th}(x,y) + (1-w) \cdot g_{ch}(x,y) \quad (6)$$

In equation (6), the symbol $g_{syn}(x, y)$ represents the pixel value of a pixel at coordinates (x, y) of the composite image, the symbol $g_{th}(x, y)$ represents the pixel value of a pixel at coordinates (x, y) of the THI image, and the symbol $g_{ch}(x, y)$ represents the pixel value of a pixel at coordinates (x, y) of the tissue characteristic image. In addition, the symbols w and (1−w) are weights assigned to the pixel value of the THI image and the pixel value of the tissue characteristic image, respectively, and 0<w<1.

On the other hand, for an area in the tissue characteristic image that includes pixels with pixel values of 0, pixel values in the THI image are assigned as they are as pixel values in the composite image.

Figure 14:
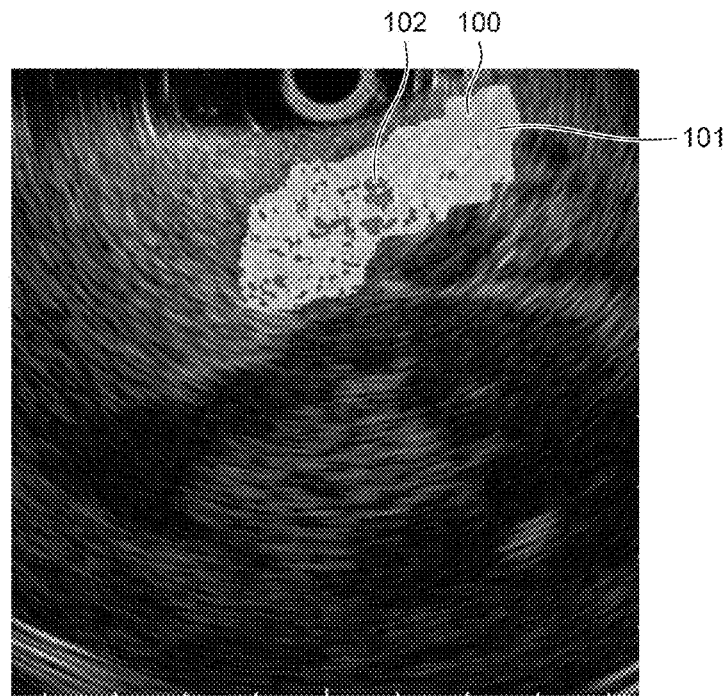
FIG. 14 is a diagram illustrating exemplary display of a composite image.
Figure 15:
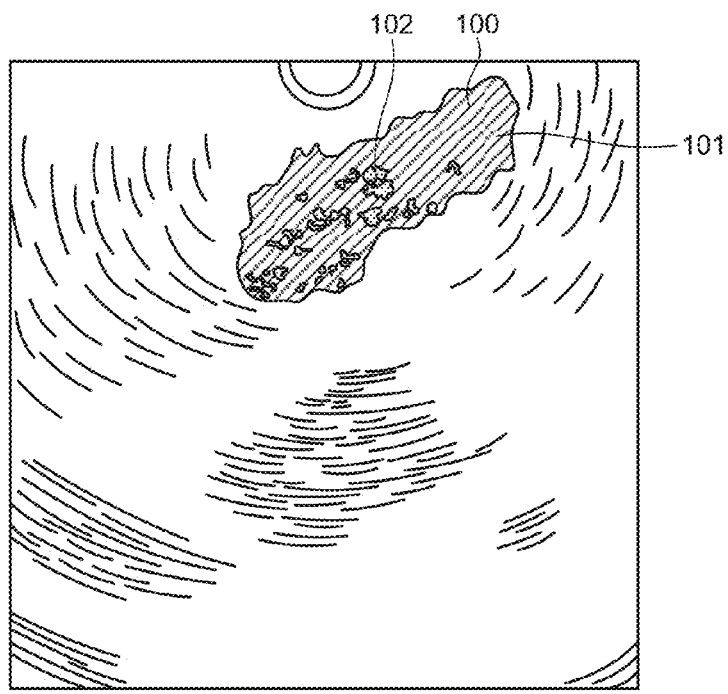
FIG. 15 is a diagram schematically illustrating the image illustrated in FIG. 14 in black and white.

At step S20, the display controller 92 displays a composite image generated based on the composite image data generated at step S19, on the display unit 7. FIG. 14 is a diagram illustrating an example of the composite image displayed at step S20. FIG. 15 is a diagram schematically illustrating the image illustrated in FIG. 14 in black and white. As illustrated in the drawings, the composite image is an image where the color tissue characteristic image (see FIG. 12) is superimposed on the grayscale THI image (see FIG. 7). An area 100 where the tissue characteristic image is superimposed is in a state in which the THI image and the tissue characteristic image are blended together by the weighted sum given by equation (6). Therefore, in the area 100, too, excellent resolution of the THI image is maintained and furthermore identification of tissue characteristics is also possible.

Figure 16:
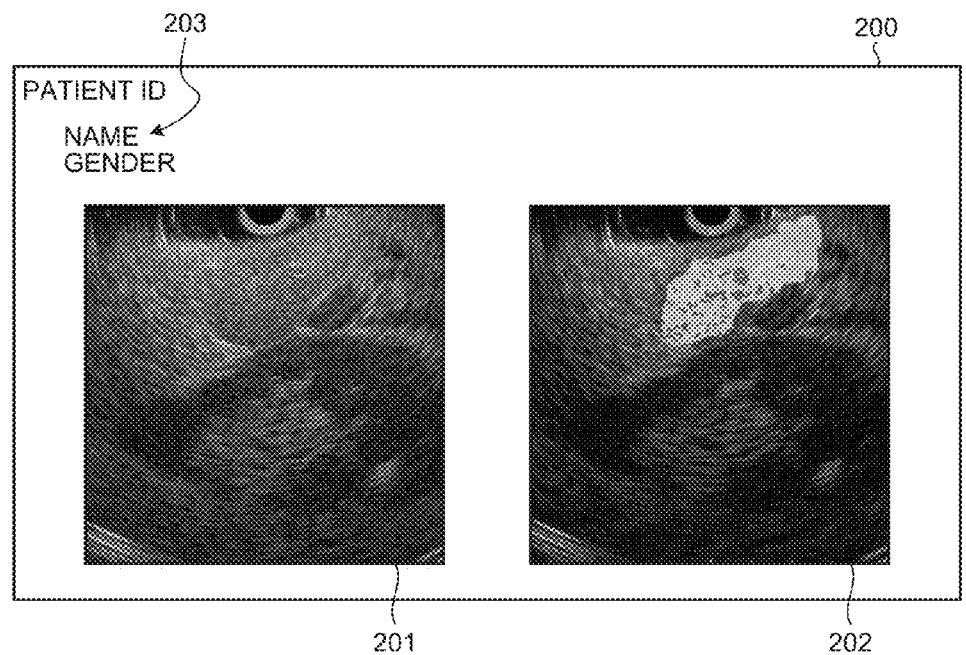
FIG. 16 is a diagram illustrating another exemplary display of the composite image.

FIG. 16 is a diagram illustrating another exemplary display of the composite image. The display controller 92 may display a screen 200 such as that illustrated in FIG. 16, on the display unit 7 using the THI image data generated at step S11 and the composite image data generated at step S19. On the screen 200, the THI image illustrated in FIG. 7 is disposed in one image display area 201, and the composite image illustrated in FIG. 14 is disposed in another image display area 202. In addition to that, a display area 203 that displays information about a patient to be examined (ID, name, gender, etc.) may be provided on the screen 200. By thus displaying the THI image and the composite image side by side, an observation method is possible where microstructures in the body are observed using the THI image and a tissue characteristic for a suspicious area is checked using the composite image. Note that exemplary display of the composite image is not limited to the above-described examples, and for example, three images including the THI image, the tissue characteristic image, and the composite image may be displayed side by side.

As described above, according to the first embodiment of the present invention, a composite image can be obtained that allows identification of tissue characteristics while using advantages of a THI image having excellent resolution and reduced artifacts. Accordingly, by referring to the composite image, an operator can grasp microstructures of body tissue and grasp differences in tissue characteristics.

In addition, according to the first embodiment, there is also an advantage in that the image quality of a tissue characteristic image itself can be improved. Here, in a conventional tissue characteristic image, noise may become large in a specific area (e.g., a blood vessel area), depending on the type of frequency feature to be used for image generation. In the first embodiment, on the other hand, first and second features are extracted from first and second sound ray data corresponding to ultrasound echoes of first and second ultrasound signals which are transmitted at different points in time, and the third feature is computed by the weighted sum of the first and second features. Thus, noise components in the feature can be reduced. Therefore, by using such third feature, a tissue characteristic image with suppressed noise can be generated.

Note that when a tissue characteristic image is generated, frequency analysis may be performed on either one of the first and second sound ray data, feature may be acquired from results of the frequency analysis, and tissue characteristic image data may be generated using the feature. In this case, calculation load of the frequency analysis unit 42 and the feature extraction unit 43 can be reduced.

In addition, the first embodiment describes an example in which two-dimensional ultrasound images (a THI image, a tissue characteristic image, and a composite image) are generated by scanning a specimen by one-dimensionally moving a line along which ultrasound signals are transmitted and received; however, three-dimensional ultrasound images may be generated by two-dimensionally scanning a specimen using, for example, a 2D array where a plurality of ultrasound transducers are arranged two-dimensionally.

First Modification

Next, a first modification of the first embodiment of the present invention will be described.

In the first embodiment, at step S18, a pixel whose third feature is smaller than the threshold is assigned a pixel value of a color according to the value of the third feature; on the other hand, depending on types of features, types of tissue to be observed, or the like, a pixel whose third feature is larger than the threshold may be assigned a pixel value of a color according to the value of the third feature. In this case, a pixel whose third feature is less than or equal to the threshold is assigned zero as a pixel value. Even when tissue characteristic image data is generated in this way, it is possible to generate and display a composite image that allows identification of tissue characteristics.

Second Modification

Next, a second modification of the first embodiment of the present invention will be described.

When a feature is extracted at step S16 illustrated in FIG. 6, attenuation correction may be performed before performing regression analysis of a frequency spectrum.

Figure 17:
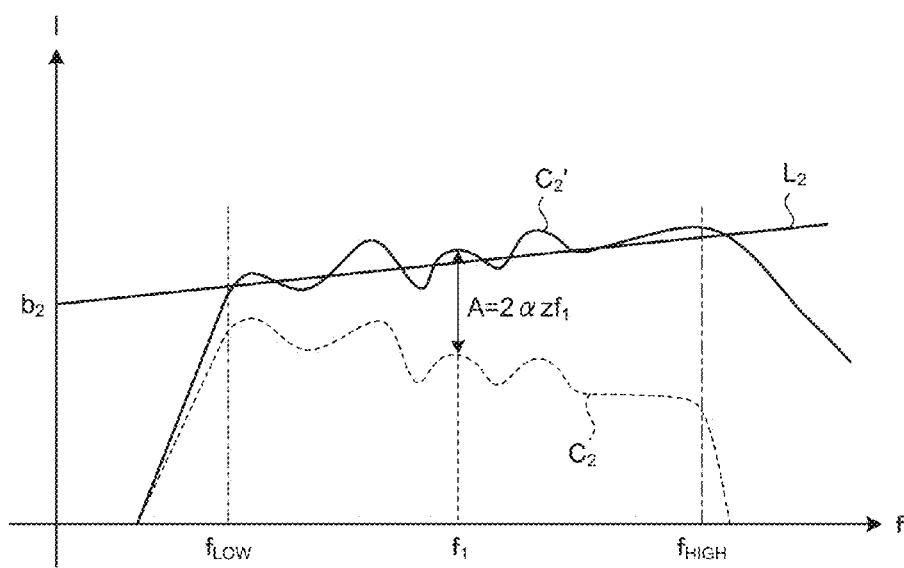
FIG. 17 is a schematic diagram for describing an attenuation correction method of a modification of the first embodiment of the present invention.

FIG. 17 is a schematic diagram for describing an attenuation correction method of the second modification. When, for example, a frequency spectrum curve $C_2$ illustrated in FIG. 17 is acquired as a result of frequency analysis at step S14, the feature extraction unit 43 performs correction where the amount of attenuation A in the above-described equation (1) is added to intensity I, on all frequencies f, and thereby obtains a new frequency spectrum curve $C_2'$. By this, a frequency spectrum where contribution of attenuation association with propagation of ultrasound is reduced can be obtained.

Thereafter, the feature extraction unit 43 performs regression analysis on the entire frequency spectrum having been subjected to the attenuation correction, and thereby extracts feature of the frequency spectrum. Specifically, the feature extraction unit 43 computes a slope a and an intercept b of a linear expression and an intensity c of a center frequency $f_{MID}$ by regression analysis on the frequency spectrum curve $C_2'$. A straight line $L_2$ illustrated in FIG. 17 is a regression line (intercept $b_2$) which is obtained by performing a feature extraction process on the frequency spectrum curve $C_2'$. By such a correction method, too, first and second features can be extracted with the same accuracy as in the first embodiment.

Second Embodiment

Next, a second embodiment of the present invention will be described. Note that a configuration of an ultrasound observation apparatus according to the second embodiment is the same as that of the first embodiment (see FIG. 1).

Although the first embodiment describes the case in which a second ultrasound signal has the same phase as a first ultrasound signal and has an amplitude that is 1/n of that of the first ultrasound signal, a combination of the first and second ultrasound signals is not limited thereto. For example, as illustrated in (a) of FIG. 18, a second ultrasound signal having the same amplitude as a first ultrasound signal (see (a) of FIG. 4) and having a phase inverted relative to that of the first ultrasound signal may be transmitted.

Figure 18:
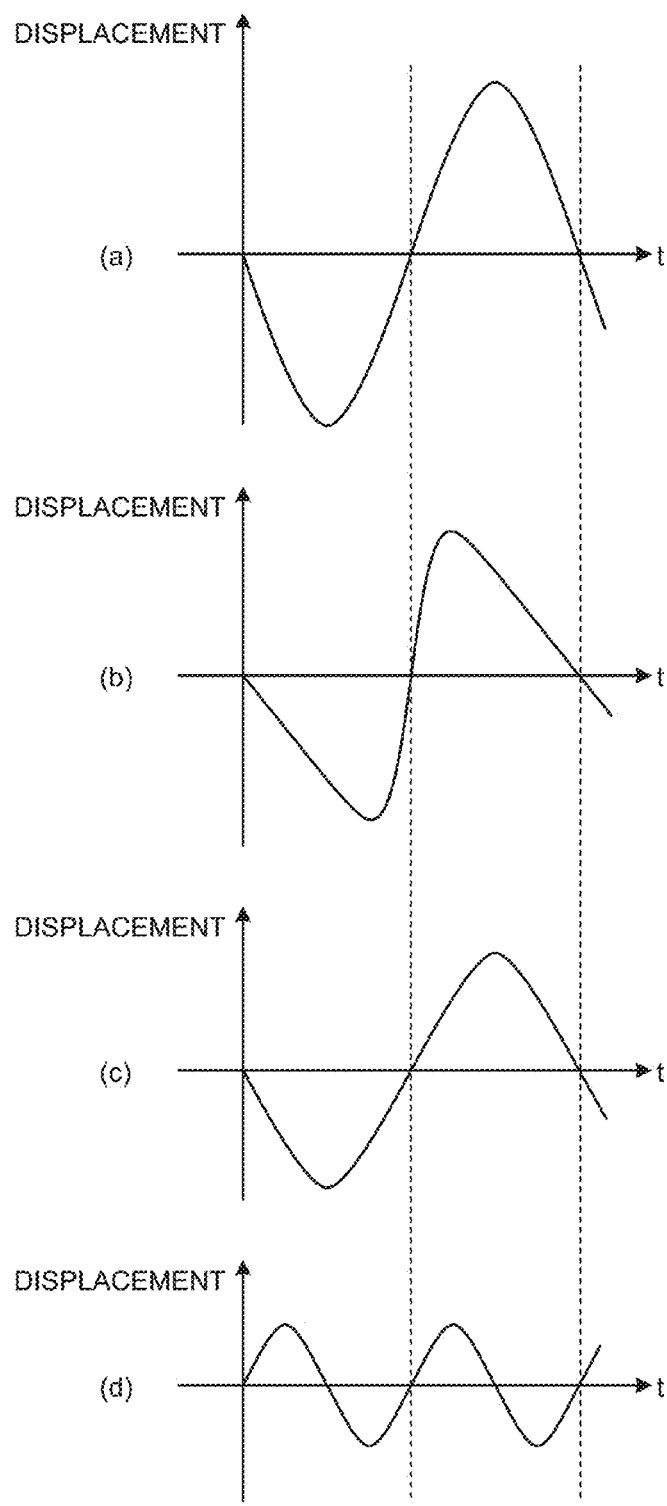
FIG. 18 is a schematic diagram illustrating examples of waveforms of a second ultrasound signal and an ultrasound echo signal thereof which are transmitted in a second embodiment of the present invention.

In this case, due to a nonlinear effect of a body signal, as illustrated in (b) of FIG. 18, distortion occurs in the waveform of a second ultrasound echo signal generated by reflection of the second ultrasound signal by a specimen. The second ultrasound echo signal can be represented as a combined wave of a fundamental wave component illustrated in (c) of FIG. 18, a second harmonic component illustrated in (d) of FIG. 18, and furthermore, a third or higher harmonic component. Hence, by adding up a first ultrasound echo signal and the second ultrasound echo signal, the fundamental wave component is cancelled out, enabling to enhance the second harmonic component.

Next, the operation of the ultrasound observation apparatus according to the second embodiment will be described with reference to FIG. 6. First, at step S10, the ultrasound observation apparatus 1 illustrated in FIG. 1 measures a new specimen by an ultrasound probe 2. At this time, the ultrasound observation apparatus 1 sequentially transmits first and second ultrasound signals having the same waveform and the same amplitude and having phases inverted relative to each other, along the same line traveling toward the specimen, and receives first and second ultrasound echo signals generated by reflection of the first and second ultrasound signals by the specimen. Operation after step S10 is the same as that of the first embodiment.

At subsequent step S11, a THI image data generation unit 51 generates THI image data based on the first and second sound ray data (received signals) which are acquired at step S10. At this time, the THI image data generation unit 51 adds up the first sound ray data (first received signal) and the second sound ray data (second received signal), and thereby generates third sound ray data (third received signal). Then, predetermined processes such as a bandpass filtering process, a detection process, and a logarithmic compression process are performed on the third sound ray data, by which THI image data is generated. Subsequent steps S12 to S14 are the same as those of the first embodiment.

At step S16 subsequent to step S14, a feature extraction unit 43 extracts a feature from each sound ray data, based on results of frequency analysis at step S14. A feature extraction process as a whole is the same as that of the first embodiment, but in the second embodiment, there is no need to perform a process where the intensities of frequency spectra which are acquired at step S14 or feature obtained after an attenuation correction process are multiplied by a factor of n, like the first embodiment. Subsequent steps S17 to S20 are the same as those of the first embodiment.

As described above, according to the second embodiment, as with the above-described first embodiment, a composite image can be obtained that allows identification of tissue characteristics while using advantages of a THI image having excellent resolution and reduced artifacts. In addition, by using a third feature image obtained by the weighted sum of the first and second features, noise in a tissue characteristic image can also be suppressed.

Third Embodiment

Next, a third embodiment of the present invention will be described. Note that a configuration of an ultrasound observation apparatus according to the third embodiment as a whole is the same as that of the first embodiment (see FIG. 1), but a tissue characteristic image data generation unit 52 does not necessarily need to be provided.

Figure 19:
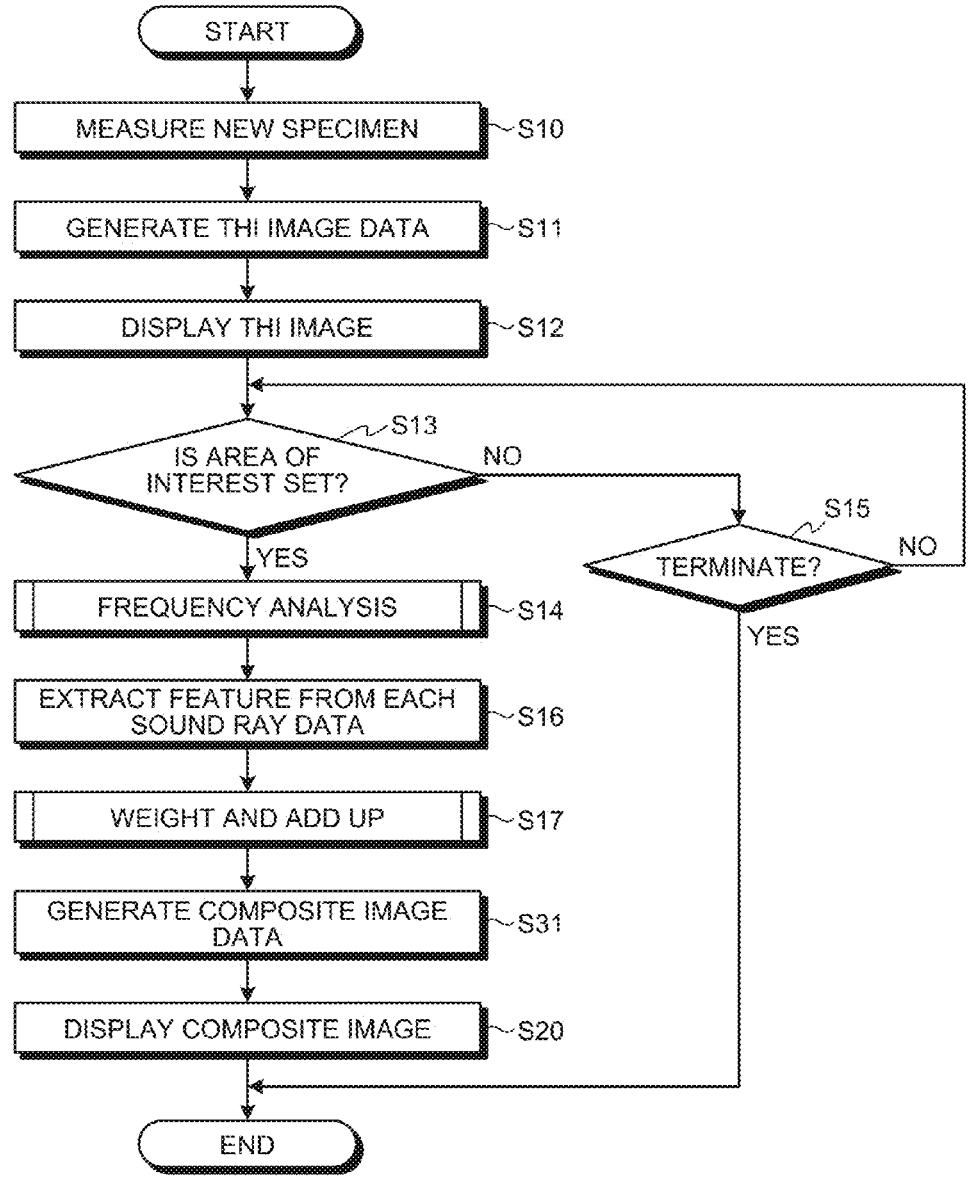
FIG. 19 is a flowchart illustrating the operation of an ultrasound observation apparatus according to a third embodiment of the present invention.

FIG. 19 is a flowchart illustrating the operation of the ultrasound observation apparatus according to the third embodiment of the present invention. Note that steps S10 to S17 illustrated in FIG. 19 are the same as those of the first embodiment. Alternatively, for steps S10, S11, and S16, those of the second embodiment may be applied.

At step S31 subsequent to step S17, an image composition unit 53 generates composite image data, using THI image data generated at step S11 and the third feature computed at step S17. More specifically, the image composition unit 53 first performs a threshold process on the third feature and thereby extracts an area including pixels whose third feature is smaller than a predetermined threshold. Then, for pixels in a THI image corresponding to respective pixel positions in the extracted area, the percentage of R, G, and B components is changed according to the value of the third feature. Namely, the hue of a pixel that is originally a grayscale pixel is changed such that the pixel becomes a color pixel. Note that for each pixel in the THI image corresponding to a pixel whose third feature is greater than or equal to the predetermined threshold, the pixel remains as its original grayscale pixel. Subsequent step S20 is the same as that of the first embodiment.

By such a technique, too, an image can be generated that allows identification of tissue characteristics while maintaining excellent resolution of a THI image.

According to some embodiments, an ultrasound image having excellent resolution is generated using a third received signal, and image data of a composite image is generated using the ultrasound image. The composite image has a display mode different from that of the ultrasound image at a pixel position where a feature extracted from frequency spectra of ultrasound echo signals satisfies a predetermined condition, and has the same display mode as that of the ultrasound image at other pixel positions. Thus, it is possible to generate the ultrasound image that allows identification of tissue characteristics and that has excellent resolution.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound observation apparatus comprising:
   an ultrasound probe configured to transmit a first ultrasound signal and a second ultrasound signal to a specimen along a same line, and to receive first and second ultrasound echo signals generated by reflection of the first and second ultrasound signals from the specimen, the second ultrasound signal having a different phase or amplitude from the first ultrasound signal; and
   a processor comprising hardware, wherein the processor is configured to:
      perform a calculation process on first and second received signals, which respectively correspond to the first and second ultrasound echo signals, to compute a third received signal, and to generate image data of a first ultrasound image having a predetermined display mode, using the third received signal;
      calculate a first feature based on a frequency spectrum of the first ultrasound echo signal;
      calculate a second feature based on a frequency spectrum of the second ultrasound echo signal;
      extract a third feature from the calculated first and second features so as to be associated with a pixel position in the first ultrasound image;
      generate image data of a second ultrasound image having a second display mode different from the predetermined display mode, at one of a pixel position where the third feature is not less than a predetermined threshold, and a pixel position where the third feature is not more than the predetermined threshold; and
      generate image data of a composite image by combining the first ultrasound image with the second ultrasound image at the one of the pixel position where the third feature is not less than the predetermined threshold, and the pixel position where the third feature is not more than the predetermined threshold.

2. The ultrasound observation apparatus according to claim 1,
   wherein the processor is configured to calculate a weighted sum of the first and second features using positive weights to extract the third feature.

3. The ultrasound observation apparatus according to claim 1,
   wherein the predetermined display mode is grayscale display,
   wherein the second display mode is color display, and
   wherein the processor is configured to:
      assign a pixel value of zero to a first pixel whose third feature in the second ultrasound image is the one of not less than the predetermined threshold, and not more than the predetermined threshold; and
      assign a pixel value of a color according to the third feature to a second pixel other than the first pixel in the second ultrasound image.

4. The ultrasound observation apparatus according to claim 3,
   wherein the processor is configured to:
      assign a pixel value of the first pixel in the first ultrasound image, to a pixel in the composite image at a corresponding position to the first pixel; and
      assign a pixel value obtained by a weighted sum of pixel values of pixels in the first ultrasound image and the second ultrasound image at corresponding positions, to a pixel in the composite image at a corresponding position to the second pixel.

5. The ultrasound observation apparatus according to claim 1,
   wherein the predetermined display mode is grayscale display, and
   wherein, for a pixel in the first ultrasound image corresponding to a pixel position other than the one of the pixel position where the third feature is not less than the predetermined threshold, and the pixel position where the third feature is not more than the predetermined threshold, the processor is configured to change a percentage of each color component in the grayscale display according to a value of the third feature to generate the image data of the composite image.

6. The ultrasound observation apparatus according to claim 1,
   wherein the processor is configured to control a display to display the composite image.

7. The ultrasound observation apparatus according to claim 6,
   wherein the processor is configured to control the display to display the composite image and the first ultrasound image side by side.

8. The ultrasound observation apparatus according to claim 1,
   wherein the second ultrasound signal has a same phase as that of the first ultrasound signal and has an amplitude that is 1/n of an amplitude of the first ultrasound signal, wherein n>0 and n≠1, and
   wherein the processor is configured to compute the third received signal by multiplying the second received signal by a factor of n and subtracting the resulting second received signal from the first received signal.

9. The ultrasound observation apparatus according to claim 1,
   wherein the second ultrasound signal has a same amplitude as that of the first ultrasound signal and has a phase inverted relative to a phase of the first ultrasound signal, and
   wherein the processor is configured to generate the third received signal by adding up the first and second received signals.

10. A method for operating an ultrasound observation apparatus, the ultrasound observation apparatus comprising: an ultrasound probe configured to transmit a first ultrasound signal and a second ultrasound signal to a specimen along a same line, and to receive first and second ultrasound echo signals generated by reflection of the first and second ultrasound signals from the specimen, the second ultrasound signal having a different phase or amplitude from the first ultrasound signal; and a processor comprising hardware, the method comprising:

by the processor, performing a calculation process on first and second received signals, which respectively correspond to the first and second ultrasound echo signals, to compute a third received signal, and generating image data of a first ultrasound image having a predetermined display mode, using the third received signal;

by the processor, calculating a first feature based on a frequency spectrum of the first ultrasound echo signal;

by the processor, calculating a second feature based on a frequency spectrum of the second ultrasound echo signal;

by the processor, extracting a third feature from the calculated first and second features so as to be associated with a pixel position in the first ultrasound image;

by the processor, generating image data of a second ultrasound image having a second display mode different from the predetermined display mode, at one of a pixel position where the third feature is not less than a predetermined threshold, and a pixel position where the third feature is not more than the predetermined threshold; and by the processor, generating image data of a composite image by combining the first ultrasound image with the second ultrasound image at the one of the pixel position where the third feature is not less than the predetermined threshold, and the pixel position where the third feature is not more than the predetermined threshold.

11. A non-transitory computer-readable recording medium with an executable program for an ultrasound observation apparatus stored thereon, the ultrasound observation apparatus comprising: an ultrasound probe configured to transmit a first ultrasound signal and a second ultrasound signal to a specimen along a same line, and to receive first and second ultrasound echo signals generated by reflection of the first and second ultrasound signals from the specimen, the second ultrasound signal having a different phase or amplitude from the first ultrasound signal; and a processor comprising hardware, the program instructing the processor to execute:

performing a calculation process on first and second received signals, which respectively correspond to the first and second ultrasound echo signals, to compute a third received signal, and generating image data of a first ultrasound image having a predetermined display mode, using the third received signal;

calculating a first feature based on a frequency spectrum of the first ultrasound echo signal;

calculating a second feature based on a frequency spectrum of the second ultrasound echo signal;

extracting a third feature from the calculated first and second features so as to be associated with a pixel position in the first ultrasound image;

generating image data of a second ultrasound image having a second display mode different from the predetermined display mode, at one of a pixel position where the third feature is not less than a predetermined threshold, and a pixel position where the third feature is not more than the predetermined threshold; and generating image data of a composite image by combining the first ultrasound image with the second ultrasound image at the one of the pixel position where the third feature is not less than the predetermined threshold, and the pixel position where the third feature is not more than the predetermined threshold.

* * * * *